United States Patent [19]

Maillard et al.

[11] 4,419,449

[45] Dec. 6, 1983

[54] PROCESS FOR THE PRODUCTION OF A SUBSTANCE HAVING BACTERIOSTATIC ACTIVITY

[75] Inventors: François Maillard; David Shepherd, both of Morges, Switzerland

[73] Assignee: Societe d'Assistance Technique pour Produits Nestle S.A., Lausanne, Switzerland

[21] Appl. No.: 230,421

[22] Filed: Feb. 2, 1981

Related U.S. Application Data

[63] Continuation of Ser. No. 86,277, Oct. 19, 1979, abandoned.

[30] Foreign Application Priority Data

Nov. 1, 1978 [CH] Switzerland .................. 11230/78

[51] Int. Cl.³ .................. C12P 1/04; C12Q 1/24; C12N 1/20; C12N 1/02

[52] U.S. Cl. .................. 435/170; 435/30; 435/253; 435/261

[58] Field of Search .................. 435/170, 261, 30, 253

[56] References Cited

PUBLICATIONS

Faust et al., J. of Bacteriology, vol. 81, pp. 99–106, (1961).
Burton et al., J. of Bacteriology, vol. 88, pp. 1775–1781, (1964).

*Primary Examiner*—Alvin E. Tanenholtz
*Attorney, Agent, or Firm*—Vogt & O'Donnell

[57] ABSTRACT

A micro-organism of the Beggiatoa type is cultured with agitation under aerobic conditions in an aqueous nutrient medium and the biomass and/or the culture medium is collected. The micro-organism used may be obtained from baregine. The bacteriostatic substance produced may be used for skin massages or as an ingredient for a cosmetic product, for example for the skin.

5 Claims, No Drawings

PROCESS FOR THE PRODUCTION OF A SUBSTANCE HAVING BACTERIOSTATIC ACTIVITY

This is a continuation, of application Ser. No. 086,277, filed Oct. 19, 1979 and now abandoned.

This invention relates to a process for the production of a substance having bacteriostatic activity.

Numerous sulphurous thermal springs in Europe contain micro-organisms which, when they accumulate in a place where the water current is weak, form a white to light grey gelatinous substance which has been given the name of "baregine" in reference to the thermal water of Bareges, a French spa in the Pyrenees. Baregine may be defined as an association of various bacteria which fix hydrogen sulphide and which are able to withstand high temperatures. Some of these bacteria are capable of secreting a mucilage with which the association as a whole is coated. Baregine contains as many dead as living elements.

The therapeutic properties of baregine have been recognised for some time and it was used at a very early stage for the treatment of rheumatic disorders by massage and for the treatment of certain skin diseases. It is an ingredient in the composition of cosmetic skin-care products.

Its production and collection have been the subject of patents relating particularly to its culture under natural conditions by various trickling processes using spring water. A similar process is currently in use at the Thermes Nationaux d'Aix-les-Bains in France. The apparatus used consists of a vertical concrete wall provided at its top with a gutter. The hot spring water brought by pipeline from the very closely situated spring runs into the gutter and trickles down the sides of the wall. The flakes of baregine, which are of the order of one centimeter in size, attach themselves to the rough parts of the concrete. A gelatinous film of baregine grows from the attached flakes and is periodically collected by scraping the wall with a hard brush. The temperature of the water and the premises in which this wall is installed is close to the emergence temperature at the spring, i.e. of the order of from 43° to 47° C. The production yield is extremely low. It rises to approximately 5 g of dry weight of baregine per square meter per month. In addition, it is subject to variations in numerous factors depending on the meteorological conditions.

Baregine has been the subject of microbiological and biochemical studies. These studies have shown the metabolism of $H_2S$ and sulphur-containing compounds, but have not elucidated the origin of the therapeutic properties of baregine. Among the numerous microorganisms identified in baregine, Beggiatoa is often mentioned. The rare isolations of Beggiatoa known from publications have, however, never been made from baregine, but instead from sludges and used waters. In addition, these isolations have proved to be laborious and difficult and the culture of the isolated microorganisms has only produced very poor yields owing inter alia to their fragility and their very high water content. A published value of 1.2 g of fresh weight of microorganisms produced without agitation over a period of 48 hours at 28° C. per liter of a culture medium containing 2 g of yeast extract, 0.1 g of sodium acetate and active catalase may be considered as characteristic.

An object of the present invention is to enable a substance having a bacteriostatic activity similar to that of baregine to be economically produced on an industrial scale.

The process according to the present invention is characterised in that a micro-organism of the Beggiatoa type is cultured with agitation under aerobic conditions in an aqueous nutrient medium and in that the biomass and/or the culture medium is collected.

It has been found that a biomass of a microorganism of the Beggiatoa type and even the medium in which it has been produced show bacteriostatic activity. It has also been found that the fragility of the microorganism is not an obstacle to its intensive culture in a vigorously agitated medium and that it multiplies even if the filaments which it forms are broken up into numerous fragments. Thus, it is even advantageous to homogenise an inoculum of the micro-organism of the Baggiatoa type before inoculating the culture medium therewith.

The expression "micro-organism of the Beggiatoa type" is used here deliberately and throughout the rest of this specification rather than the expression "micro-organism of the genus Beggiatoa." The genus Beggiatoa belongs to the class of "gliding bacteria", an order of the myxobacterales, a member of the family Beggiatoaceae (cf. Bergey's Manual of Determinative Bacteriology, 8th Edition, Waverly Press, Baltimore, U.S.A., 1974, pages 112–114). As can be seen from this work, which is an authority in the art, the classification of micro-organisms of this genus is largely unconfirmed in view of the scarcity of reliable information. It would be inappropriate to adopt a scientific term as precise as "genus" in view of the precariousness of the classification of the micro-organisms in question. In the context of the present invention, therefore, the expression "micro-organism of the Beggiatoa type" is understood to cover filamentous bacteria characteristic of sulphurous soils and waters of which the colourless filaments move by gliding and are formed by chains of cells, such as the bacteria classified under the genus Beggiatoa.

The micro-organism of the Beggiatoa type is preferably obtained by isolation from baregine. It has been found that isolation such as this is possible by adopting a certain procedure and that the strains which it produces may be cultureed and effectively have bacteriostatic activity. Finally, it has been found that even the problem of their preservation may be satisfactorily solved.

In order to isolate a strain, a sample of baregine may be deposited on a gelose-containing nutrient medium and incubated for form 5 to 36 hours at a temperature of from 25° to 50° C., after which a zone in which the filaments of a micro-organism of the Beggiatoa type are free from contaminants is cut out and deposited on a gelose-containing nutrient medium identical with the first. The incubation, cutting out and sub-culturing operations may be repeated two or three times.

This procedure was used for isolating the S strains which were lodged on the 12th July, 1978 in the National Collection of Industrial Bacteria (NCIB). Aberdeen, Scotland, and which have been given the numbers NCIB 114 18 to 114 25. Accordingly, the process according to the present invention may be carried out using at least one of these 8 strains for example.

The gelose-containing nutrient medium used for isolation preferably consists of from 1 to 4 g of yeast extract and from 10 to 20 g of agar per liter of water.

Similarly, the aqueous nutrient medium preferably used for culturing the micro-organisms contains from 1 to 4 g of yeast extract, from 0.1 to 0.3 g of calcium chloride and from 0.2 to 1 g of sodium or ammonium acetate per liter of water. The water used is preferably sulphurous thermal water. To protect the culture, catalase may also be added to the medium for example in a quantity of from 5 to 20 international units (IU) per ml. The micro-organism may be cultured over a period of from 5 to 36 hours at a temperature of from 20° to 50° C. and at a pH-value of from 6 to 8. It is preferably cultured over a period of from 8 to 10 hours at a temperature of from 30° to 40° C. and at a neutral pH-value.

The bacteriostatically active substance obtained by the process according to the present invention may be used as such for skin massages or as an ingredient of a cosmetic product for the skin for example. The biomass may be conserved in a dried form. It is preferably dried by freeze-drying in view of its fragility and its low dry matter content.

The following Examples given by way of illustration will enable the nature and scope of the present invention to be better understood. In the following Examples, the name "Beggiatoa" is systematically used in place of, but is understood to be synonymous with, the expression "micro-organism of the Beggiatoa type."

EXAMPLE 1 (ISOLATION OF THE STRAINS)

A flake of fresh baregine taken from the Thermes Nationaux d'Aix-les-Bains is placed in the centre of a Petri dish containing 20 ml of gelose medium prepared in accordance with the following recipe:

| | |
|---|---|
| Yeast extract (Difco) | 2 g |
| Agar (Bacto-Difico) | 15 g |
| Filtered thermal water from Aix | 100 ml |
| Distilled water | 900 ml |

The dish is placed upside down in an oven at 30° C. for 30 hours. It is then examined under a microscope (low magnification) to detect the presence of spiral structures characteristic of Beggiatoa and resulting from the mobility of these microorganisms by gliding. Some are even visible with the naked eye. The microscopic examination also reveals zones in which the filaments of Beggiatoa seem free from contaminants. One of these zones is cut out using a sterile scalpel and placed on a fresh agar plate having the same composition as the first, taking care to apply the surface containing the filaments of Beggiatoa to the clean surface of the new agar plate. The whole is then re-incubated for 24 hours at 30° C. The operation is cutting out, sub-culturing and incubation is repeated twice more. A pure culture of Beggiatoa is obtained.

EXAMPLE 2 (CONSERVATION OF THE STRAINS)

Ten strains are isolated in the manner described in Example 1. They differ from one another in the diameter of their filaments, their gliding speed and the form of their colonies on agar. They are successfully conserved in three different ways, depending on whether short-term, medium-term or long-term conservation is required.

(2.1.) short-term: the plate is kept in a refrigerator at 4° C., taking care to seal the Petri dish. The strain is transferred every 10 days because agar has a tendency to dry out.

(2.2.) medium-term: a semi-liquid medium having the following composition is prepared:

| | |
|---|---|
| Yeast extract | 2 g |
| $CaCl_2$ | 0.1 g |
| Sodium acetate | 0.5 g |
| Agar | 2 g |
| Filtered thermal water | 1000 ml |

After sterilisation of the medium, fungal catalase is added to it in a quantity of 10 IU/ml. The catalase solution is sterilised beforehand by cold filtration on a Millipore filter having microscopic pores $0.22\mu$ in diameter.

A small cube of agar containing Beggiatoa is placed in a tube containing 10 ml of medium and incubated at 30° C. The Beggiatoa develops in the upper part of the tube. The tube is left for 3 weeks at 30° C. The culture is then transferred in a quantity of 0.1 ml per tube.

(2.3.) long-term: a 24-hour culture is prepared in agitated medium in the same way as described in Example 3. After centrifuging, the deposit is washed with sterile Ringer's solution. The deposit is frozen and freeze-dried. It is stored for several months in a refrigerator in a tightly sealed container. On rehydration, the fragments of filaments are capable of developing.

EXAMPLE 3 (CULTURE OF THE STRAINS)

3.1. Inoculum

A small cube of agar (5 $mm^3$) is cut out from a plate obtained in the manner described in Example 1. It is placed in a 500 ml bottle containing 100 ml of the following medium:

| | |
|---|---|
| Yeast extract | 4 g |
| Calcium chloride | 0.2 g |
| Ammonium acetate | 1 g |
| Filtered thermal water | 1000 ml |

This medium has a pH-value of 6.6. The bottle is placed in an orbital agitator rotating at 150 revolutions per minute for a radius of gyration of 1.25 cm and left there for 16 hours at 30° C. The culture obtained is homogenised for from 15 to 30 seconds under sterile conditions in a Sorvall Omnimixer. The homogenised culture constitutes the inoculum.

3.2. Culture 5 ml of the above inoculum are introduced into a 500 ml bottle containing 100 ml of the same medium as used for preparation of the inoculum. The bottle is incubated for 24 hours at 30° C. in the orbital agitator. 0.8 g of dry matter of Beggiatoa per liter of culture is obtained. By repeating the operation with various strains and by varying the conditions within the stated limits, yields of from 1.25 to 2 g of dry Beggiatoa per liter of culture are obtained.

3.3. Measurement of growth:

The conventional method of nephelometry applied to bacterial cultures cannot be used for Beggiatoa on account of its flake-like growth. It is adapted to the particular case. Culture samples are taken every 2 hours and homogenised using a Sorvall Omnimixer. Their optical density at 600 nm is determined using a spectrophotometer. The homogenised sample sediments only slowly and allows a reliable reading to be obtained. An indication of the growth is thus obtained in direct relation to the number of cells.

3.4. Determination of the dry weight:

Conventional drying in an oven does not give reproducible results in the case of Beggiatoa. This is probably due to its very high water content. It is for this reason that, in order to obtain reproducible results, quantities of never less than 400 ml of culture are dried by freeze-drying.

3.5. Determination of the bacteriostatic activity:

The conventional method of evaluating bacteriostatic activity developed by the *Public Health Laboratory Service Committee* and described in the British Med. J. 408 (1965) does not given satisfactory results in the particular case of Beggiatoa because the test is carried out in tubes. Since Beggiatoa is strictly aerobic, the concentration of oxygen available in a test tube is inadequate. Accordingly, the method is adapted and agitated bottles are used to increase the transfer of oxygen.

Three series of 50 ml bottles each containing 18 ml of nutrient broth (Nutrient Broth Difco) are prepared. The bottles of the first and second series are each inoculated with 0.4 ml of a 24-hour culture of a pathogenic strain. Three pathogenic strains are used, namely *Pseudomonas aeruginosa* ATCC 10145, *Escherichia coli* ATCC 11755 and *Staphylococcus aureus* ATCC 12600.

Samples of bacteriostatic product are prepared by centrifuging a culture obtained in the manner described in Example 3.2., but for 8 hours only. The centrifuged biomass is homogenised and resuspended in a volume of physiological solution equal to the volume of the supernatant phase left after centrifuging. The physiological solution containing the biomass and the supernatant phase are each divided into 2 ml samples.

2 ml of physiological solution containing the homogenised biomass are added to the bottles of the first series. 2 ml of physiological solution alone are added to the bottles of the second series. 2 ml of physiological solution containing the homogenised biomass are added to the bottles of the third series which have not been inoculated with a pathogen.

The bottles are incubated at 37° C. in an orbital agitator. Their optical density at 600 nm is measured after 16 hours. The optical density measurements of the corresponding bottles of the first, second and third series are represented by the respective parameters A, B and C. The difference A-C subtracted from B and then divided by 8 and multiplied by 100 gives the bacteriostatic activity of the biomass as percentage inhibition.

The bacteriostatic activity of the supernatant phase is determined in the same way by adding 2 ml of supernatant phase instead of 2 ml of physiological solution containing the homogenised biomass to the bottles of the first and third series.

The results are set out in the following Table:

| Pathogenic agent | Activity of the biomass (% inhibition) | Activity of the supernatant phase (% inhibition) |
| --- | --- | --- |
| P. aeruginosa | 70 | 41 |
| S. aureus | 100 | 45 |
| E. coli | 70 | 11 |

EXAMPLE 4 (COMPARISON)

The bacteriostatic activity of natural baregine is determined for comparison in the manner described in Example 3.5. Percentage inhibitions of 100%, 83% and 96% with respect to *P. aeruginosa*, *S. aurcus* and *E. coli*, respectively, are observed after incubation for 16 hours. In other words, the bacteriostatic activity of the biomass according to the present invention is almost as strong as that of baregine. This is a remarkable result considering that the biomass according to the present invention may be industrially produced in a high yield whereas baregine can only be obtained slowly and in very small quantities. The activity of the supernatant according to the present invention, although lower, is nonetheless interesting.

EXAMPLE 5 (NCLB STRAINS)

8 strains were isolated in the manner described in Example 1. These 8 strains were lodged on the 12th July, 1978 in the National Collection of Industrial Bacteria (NCIB) in Aberdeen Scotland, and as mentioned above have been given the numbers NCIB 114 18 to 114 25. These strains may be characterised by their growth qualities, by their morphology when cultured on agar and in liquid medium and by their bacteriostatic activity.

The following Table shows the optical density of the cultures obtained after 5, 10 and 24 hours by cultivating each of these strains in the manner described in Example 3.2., the biomasses obtained after 24 hours and the bacteriostatic activity of the biomasses obtained after 8 hours' culture with respect to the 3 pathogenic strains *P. aeruginosa*, *S. aureus* and *E. coli*. The morphologies are then separately indicated for each strain.

| Strain NCIB No. | Optical Density | | | Biomass (g of dry matter/l) |
| --- | --- | --- | --- | --- |
| | after 5h | after 10h | after 24h | |
| 114 18 | 0.237 | 0.713 | 0.583 | 0.91 |
| 114 19 | 0.352 | 0.621 | 0.514 | 0.95 |
| 114 20 | 0.147 | 0.447 | 0.709 | 0.95 |
| 114 21 | 0.160 | 0.402 | 0.646 | 0.95 |
| 114 22 | 0.289 | 0.364 | 0.305 | 0.75 |
| 114 23 | 0.360 | 0.496 | 0.378 | 0.69 |
| 114 24 | 0.217 | 0.737 | 0.587 | 0.59 |
| 114 25 | 0.395 | 0.981 | 0.838 | 1.11 |

| Strain NCIB No. | Activity (% inhibition) | | |
| --- | --- | --- | --- |
| | P. aeruginosa | S. aureus | E. coli |
| 114 18 | 100 | 76 | 100 |
| 114 19 | 100 | 96 | 74 |
| 114 20 | 100 | 96 | 44 |
| 114 21 | 100 | 98 | 100 |
| 114 22 | 68 | 89 | 84 |
| 114 23 | 73 | 87 | 25 |
| 114 24 | 57 | 80 | 27 |
| 114 25 | 100 | 91 | 90 |

MORPHOLOGIES

NCIB 114 18:

On agar: forms large isolated colonies from 8 to 15 mm in diameter with a white centre and translucent borders. Examination by microscope (×100): the colony is formed by clearly visible, tightly coiled spirals.

In liquid culture: homogeneous culture. Examination by microscope (×400): long filaments measuring 80×1.8µ, occasionally formed by short, distinct bacilli. No aggregation. Very vew refractile inclusions.

NCIB 114 19:

On agar: forms white isolated colonies from 4 to 8 mm in diameter with diffuse borders. Thick strands extend radially in the shape of a star from the centre of the colony, but do no reach its borders. Examination by microscope (×100): the borders of the colony are formed by tightly coiled filaments.

In liquid culture: homogeneous culture. Examination by microscope (×400): very short isolated filaments measuring 3.6×0.9μ divided by very clear constrictions. No refractory inclusions. Forms aggregates.

NCIB 114 20:

On agar: forms flat, opaque isolated colonies from 2 to 5 mm in diameter with fringed borders. Examination by microscope (×100): colonies formed by fragments of filaments in the form of poorly developed spirals.

In liquid culture: homogeneous culture. Examination by microscope (×400): no filaments. Long bacilli measuring 9×1.4μ containing a few refractile inclusions.

NCIB 114 21:

On agar: forms separate colonies from 4 to 7 mm in diameter with diffuse border very similar to those of the strain NCIB 114, 19, but whiter. The borders of the colonies are translucent. Examination by microscope (×100): no visible spirals.

In liquid culture: homogeneous culture. Examination by microscope (×400): image similar to that presented by the strain NCIB 114 20. No filaments, long bacilli measuring 18×1.4μ containing a few refractile inclusions. No aggregates.

NCIB 114 22:

On agar: never forms isolated colonies. Covers the entire surface with translucent mycoid strands Examination by microscope (×100): strands formed by several filaments.

In liquid culture: homogeneous culture showing a few small aggregates from the 6th hour. Examination by microscope (×400): long separated filaments measuring 90×1.4 to 1.8μ. Filaments divided into long units by distinct constrictions. Very few refractile inclusions.

NCIB 114 23:

On agar: similar to the strain NCIB 114 22. No isolated colonies. Dense and more clearly visible mycoid bands. Examination by microscope (×100): more distinct strands because they are formed by a larger number of filaments.

In liquid culture: forms large flakes (aggregates). Examination by microscope (×400): much shorter filaments than those of the strain NCIB 114 22 divided into segments by very clear constrictions. Length 9 to 10×1.8μ. Refractile inclusions appear very quickly after 5 hours.

NCIB 114 24:

On agar: similar to the strain NCIB 114 23. No isolated colonies. Mycoid strands, Examination by microscope (×100): strands formed by a large number of filaments.

In liquid culture: forms large flakes (aggregates). Examination by microscope (×400): long filaments measuring 140×1.8μ which form long bundles. No visible constrictions. Late development (after 10 hours) of refractile inclusions.

NCIB 114 25:

On agar: forms opaque isolated colonies from 2 to 6 mm in diameter. Examination by microscope (×100): colonies formed by filaments consisting of isolated cells and forming tight spirals.

In liquid culture: homogeneous culture. Examination by microscope (×400): short homogeneous filaments measuring 4×1.4μ. Few refractile inclusions.

We claim:

1. A process for the production of a substance having bacteriostatic activity, which comprises isolating one or more strains of Beggiatoa micro-organisms selected from the group consisting of the strains NCIB 114 18 to NCIB 114 25 from baregine, culturing the micro-organisms with agitation under aerobic conditions over a period of from 5 to 36 hours at a temperature of from 20° to 50° C. and at a pH-value of from 6 to 8 in an aqueous nutrient medium and collecting the biomass and/or the culture medium.

2. A process as claimed in claim 1, wherein the micro-organism is cultured over a period of 8 to 10 hours at a temperature of from 30° to 40° C. and at a neutral pH.

3. A process as claimed in claim 1, wherein the biomass is collected and freeze-dried.

4. A process as claimed in claim 1, wherein the aqueous nutrient medium contains from 1 to 4 g of yeast extract, from 0.1 to 0.3 g of calcium chloride and from 0.2 to 1 g of sodium or ammonium acetate per liter of water.

5. A process as claimed in claim 4, wherein the water is a sulphurous thermal water.

* * * * *

UNITED STATES PATENT AND TRADEMARK OFFICE
CERTIFICATE OF CORRECTION

PATENT NO. : 4,419,449
DATED : December 6, 1983
INVENTOR(S) : Francois Maillard, et al.

It is certified that error appears in the above—identified patent and that said Letters Patent is hereby corrected as shown below:

Column 2, line 52, "form" should read -- from--.

Column 2, line 59, "S" should read --8--.

Column 2, line 61, after "(NCIB)", the period should be a comma.

Signed and Sealed this

Twenty-eighth Day of February 1984

[SEAL]

Attest:

GERALD J. MOSSINGHOFF

Attesting Officer      Commissioner of Patents and Trademarks